(12) United States Patent
Plank

(10) Patent No.: US 8,215,800 B2
(45) Date of Patent: Jul. 10, 2012

(54) SEMICONDUCTOR RADIATION SOURCE

(75) Inventor: Wolfgang Plank, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 210 days.

(21) Appl. No.: 12/587,796

(22) Filed: Oct. 13, 2009

(65) Prior Publication Data
US 2010/0135018 A1 Jun. 3, 2010

(30) Foreign Application Priority Data

Oct. 10, 2008 (DE) .................. 10 2008 051 256

(51) Int. Cl.
*F21V 29/00* (2006.01)
(52) U.S. Cl. ............... 362/294; 362/373; 362/249.02
(58) Field of Classification Search ............ 362/294, 362/373, 249.02, 573, 231; 361/719, 749; 174/254; 349/150
See application file for complete search history.

(56) References Cited

U.S. PATENT DOCUMENTS

| | | | |
|---|---|---|---|
| 6,331,111 B1 | 12/2001 | Cao | |
| 6,867,377 B2* | 3/2005 | Anderson et al. | 174/254 |
| 6,991,456 B2* | 1/2006 | Plank | 433/29 |
| 7,086,767 B2* | 8/2006 | Sidwell et al. | 362/545 |
| 7,466,076 B2* | 12/2008 | Lin et al. | 313/512 |
| 7,600,890 B2* | 10/2009 | Swantner et al. | 362/228 |
| 7,679,672 B2* | 3/2010 | Chua et al. | 348/371 |
| 7,736,019 B2* | 6/2010 | Shimada et al. | 362/244 |
| 7,766,509 B1* | 8/2010 | Laporte | 362/249.02 |
| 7,852,425 B2* | 12/2010 | Nishimura | 349/58 |
| 7,943,941 B2* | 5/2011 | Shimizu et al. | 257/89 |
| 2002/0151941 A1 | 10/2002 | Okawa | |
| 2003/0107885 A1* | 6/2003 | Galli | 362/205 |
| 2005/0135094 A1 | 6/2005 | Lee | |
| 2006/0264093 A1* | 11/2006 | Shim | 439/495 |
| 2008/0289859 A1* | 11/2008 | Mikado et al. | 174/254 |
| 2009/0040415 A1* | 2/2009 | Kim | 349/56 |
| 2009/0141500 A1* | 6/2009 | Peng | 362/294 |

FOREIGN PATENT DOCUMENTS

| | | |
|---|---|---|
| DE | 10216618 A1 | 1/2003 |
| DE | 10242366 A1 | 4/2004 |
| DE | 10350913 A1 | 6/2005 |
| EP | 0777276 A2 | 6/1997 |
| EP | 1046859 A1 | 10/2000 |
| EP | 1465256 A1 | 10/2004 |
| JP | 2000188001 A | 7/2000 |

\* cited by examiner

*Primary Examiner* — Peggy A. Neils
(74) *Attorney, Agent, or Firm* — Ann M. Knab; Thad McMurray

(57) ABSTRACT

The invention relates to a semiconductor radiation source comprising a base body which is connected to at least one LED chip thermally connected to an end side of the base body and a pliable flexible printed circuit board fitted on the same end side of the base body. The flexible printed circuit board at least partly surrounds the LED chip, has at least one printed-on conductor track (20) electrically connected to the LED chip and, in the peripheral region of the base body, has an angled-away section (27) extending at least partly along a side wall of the base body. At least one part of the section of the flexible printed circuit board (14) extends at least partly in an in particular lateral cutout (34) into the base body (12).

22 Claims, 3 Drawing Sheets

SEMICONDUCTOR RADIATION SOURCE

CROSS-REFERENCE TO RELATED APPLICATIONS

This application claims foreign priority benefits under 35 U.S.C. §119(a)-(d) from German patent application ser. no. P 10 2008 051 256.7 filed Oct. 10, 2008.

TECHNICAL FIELD

The invention relates to a semiconductor radiation source comprising a base body, at least one LED chip thermally connected to an end side of the base body, and a pliable flexible printed circuit board fitted on the same end side of the base body.

BACKGROUND OF THE INVENTION

A semiconductor radiation source of this type is known from DE 102 42 366 A1. In the case of a semiconductor radiation source of this type, currents of considerable magnitude can be fed to the radiation source in order to provide the desired light power. This necessitates firstly good cooling, but secondly also corresponding cross-sectional dimensions for the feed lines. The document cited discloses the use of a flexible carrier layer composed of its insulating material for the configuration of a printed circuit.

This semiconductor radiation source uses a flexible carrier layer that is specially adapted such that it can for example also follow a round form such as that of the cooling rod there, in the course of bending away over the front edge. Therefore, such a flexible carrier layer requires particularly high elasticity, which inherently runs counter to the properties of the conductor tracks used. In particular, large line cross sections cannot be accommodated in elastic-flexible solutions of this type.

OBJECTS AND SUMMARY OF THE INVENTION

Against this background, the invention is based on the object of configuring a semiconductor radiation source that is suitable in particular for a light curing device for dental technology such that high power in conjunction with good cooling of the semiconductor chips used is combined with a compact arrangement that is also adaptable for different power levels.

The object is achieved according to the invention by means of providing a base body, at least one LED chip thermally connected to an end side of the base body, and a pliable flexible printed circuit board fitted on the same end side of the base body, wherein the flexible printed circuit board at least partly surrounds the LED chip, has at least one printed-on conductor track (20) electrically connected to the LED chip and, in the peripheral region of the base body, has an angled-away or bent-away section (27) extending at least partly along a side wall of the base body, wherein at least one part of the section (27) of the flexible printed circuit board (14) extends at least partly in an in particular lateral cutout (34) into the base body (12).

The arrangement of a flexible printed circuit board known per se areally on the surface of a heat sink on which the LED chips are also supported gives rise firstly to the possibility of permitting the flexible printed circuit board to extend over the entire width of a side edge of the heat sink. As a result of this, the flexible printed circuit board can be easily bent over there, such that electrical conductor tracks can extend toward the rear without appreciable restrictions with regard to the current consumption capacity and can thus serve for the current supply also for example of LED chips with higher power.

In an advantageous configuration it is possible according to the invention to bend over the flexible printed circuit board doubly as it were and to permit it to extend in this way into a cutout extending behind the primary heat sink carrying the LED chips. This opens up the possibility of accommodating electrical components there such that they are accommodated in protected fashion and in concealed fashion, without the heat dissipation being impaired.

By virtue of the fact that the flexible printed circuit board extends over an outer edge of the substantially parallelepiped base body, there is the possibility of providing a very large accommodating width for the conductor tracks. This enables a comparatively large cross section per conductor track, in combination with the very large thickness of the conductor tracks, which can even be more than 0.035 mm, for example only 0.07 mm.

The U-shaped support of the base body results firstly in an also laterally stiff support on lateral column-shaped sections of a heat dissipating body carrying the end body. In addition, the column-shaped sections lie free laterally, such that their surfaces can at the same time be used as cooling areas.

By means of the skillful combination of the end body with the heat dissipating body for forming the base body, it is possible firstly to accommodate the rather sensitive flexible printed circuit board in protected fashion and likewise to accommodate electronic components in protected fashion. The large-area cutout also makes it possible to accommodate the electronic or electrical components applied on the section of the flexible printed circuit board such that they are outside a thermal contact with the heat dissipating body and in this respect are not impaired thermally.

Preferably, a lateral incision or cutout is formed below the intrinsic base body. The incision extends advantageously from the side into the base body and/or the heat dissipating body such that an incision is provided which is accessible from the side and which offers assembly space without increasing the heat dissipation.

Preferably, the flexible printed circuit board at least partially extends around the base body, and thus is angled to more than 90° at one side of the base body. While it abuts in a flat manner on the upper side of the base body, in order to improve heat dissipation, the flexible printed circuit board may abut on the other side of the base body as well, or it may freely extend into the space of the cutout.

Hereto, the base body is in large-area contact with the heat dissipating body, e.g. surrounding the cutout at at least two sides, preferably at three sides, while the fourth side is open.

The respective portion of the flexible printed circuit board may pass through the base body, in order to extend into the cutout space. Alternatively, the base body is shortened from the outer periphery of the heat dissipating body, towards the open side of the cutout such that the flexible printed circuit board may be led around the respective lateral edge of the base body.

Yet the flexible printed circuit board preferably extends within the outer periphery of the heat dissipating body—at least in the axial projection—such that the flexible printed circuit board is protected against damage.

The heat dissipation is, according to the invention, preferably such that no relevant heat resistance is provided at any point between the heat source which is formed by the LED chip or LED chips and the rear region of heat dissipating body.

The base body is preferably cuboid shaped—with exception of the cutout at its underside—namely, like a flat cuboid. The heat source is arranged on the centre of its upper side, and as the heat source rests on the upper side centrally and on a large and plain area, a good heat dissipation is ensured. The heat dissipation preferably is achieved via two or three heat dissipating legs of the base body the width of which is greater than the thickness of the rest area of the heat source on the base body such that a high heat resistance is avoided here as well.

The front side of the legs are preferably contacted by rest legs of the heat dissipating body which are at least of the same size. An ample assembly space cutout is provided although a large area contact between base body and heat dissipating body is provided.

It is to be understood that the exact form of contacting between the base body and the heat dissipating body may be adapted to the requirements in large extents. For example, the side legs of the base body but also the rest legs of the heat dissipating body may have an outer curved form following the perimeter of the heat dissipating body by which thus the heat conductance is still improved.

Also, the cutout of the heat dissipating body—and thus the cutout of the base body—are not required to have a rectangular cross section; a trapezoidal cross section or a rounded cross section is possible as well.

In so far, the relation between the area of the cutouts in the heat dissipating body and the base body and the contact surfaces may be deliberately adapted to the requirements.

In a modified configuration, the flexible printed circuit board extends over the peripheral region of the base body or ends there and is guided in a manner spaced apart from the edge through a slot into the cutout extending on the rear side of the end body. This configuration can be realized particularly when the end body and the heat dissipating body can be separated from one another. The assembly can then be effected such that firstly the flexible printed circuit board is mounted on the base body, to be precise after the flexible printed circuit board has already been populated with electrical and electronic components. By means of the assembly of the end body with the heat dissipating body, the flexible printed circuit board is then additionally protected and accommodated, wherein it goes without saying that care should be taken to ensure a low thermal resistance between end body and heat dissipating body.

According to the invention it is particularly favorable for the flexible printed circuit board to be completely releasable from the base body, which is particularly simple if the connections are held in pluggable fashion. In the event of a defect of an electronic component, a repair can thus be carried out inexpensively and in an easy-to-service manner.

According to the invention it is particularly favorable if the heat-emitting electronic or electrical components accommodated on the flexible printed circuit board are in thermal contact with the heat dissipating body, in particular at a location which is spaced apart from the end body. In the case of this arrangement, there is the possibility of utilizing the cooling effect of the heat dissipating body, which is cooler than the end body, for the cooling of the electronic components emitting power loss. Cooling fins or cooling areas cooled by convection or forced air guidance, for example by a fan, are typically provided at that end of the heat dissipating body which is remote from the end body. The cooling of the heat dissipating body at this location gives rise to a temperature gradient, the magnitude of which depends on the thermal conductivity of the heat dissipating body. By virtue of the comparatively large structural cross section of the heat dissipating body, it is possible to provide a low thermal resistance and thus a high thermal conductivity.

An advantageous configuration provides for using the base body as a conductor in a manner known per se. Particular consideration is given here to the use as a ground conductor, such that the conductor tracks accommodated on the flexible printed circuit board can be significantly enlarged in their cross section since the ground conductor is then obviated there. This measure also contributes to compactly connecting and being able to supply high-power LED chips. It goes without saying that with separate embodiment of the end body and of the heat dissipating body, care must be taken in this case to ensure that there is a low-resistance electrical connection between these bodies.

In a further advantageous configuration it is possible to provide the end body with a through hole in order to provide a transition between the front area of the end body which accommodates the flexible printed circuit board and the rear side of the end body along which the flexible printed circuit board can likewise extend. Here it is possible, whilst circumventing the deflection region of the flexible printed circuit board, to realize a plated-through hole in order, if possible, to enable a further reduction of the internal resistance of the connecting lines for the LED chips.

It goes without saying that the LED chips can be driven in any suitable manner, even indeed with a plurality of connecting lines, such that for example the outer LED chips can be driven in a different circuit than the inner LED chips.

According to the invention it is particularly favorable for the section to have a width which is smaller than a side length of the base body.

According to the invention it is particularly favorable for the section to extend along at least one part of a rear side—remote from the LED chip—of the base body, in particular the end body thereof.

According to the invention it is particularly favorable for the section to have a width which is smaller than the side length of the base body, as viewed in the direction parallel to the width, and to extend, in particular, proceeding from a front side of the base body, at least along a side wall of the base body.

According to the invention it is particularly favorable for the base body to have a lateral cutout and/or at least one through opening in which a section of the flexible printed circuit board extends.

According to the invention it is particularly favorable for the section to extend along at least one part of a rear side—remote from the LED chip—of the base body.

According to the invention it is particularly favorable for the section, in particular at least in the region of the cutout, to carry at least one electronic component such as a diode, a resistor or an ASIC, and in particular the electronic components to be accommodated in recessed fashion in the cutout.

According to the invention it is particularly favorable for the section to have a free end which projects freely from the rear side of the base body and to be in particular free of electronic components.

According to the invention it is particularly favorable for an end body of the base body to be thermally connected to a heat dissipating body.

According to the invention it is particularly favorable for the section to surround the base body substantially in U-shaped fashion and to bear areally thereon—if appropriate with interposition of an insulation.

According to the invention it is particularly favorable for the heat dissipating body to have a cutout into which projects the section, in particular the free end of the section.

According to the invention it is particularly favorable for the base body to be formed in two parts and to have an end body and a heat dissipating body which are thermally intensively connected to one another.

According to the invention it is particularly favorable for a plurality of LED chips to be fitted on the base body, wherein at least one LED chip can be driven separately.

According to the invention it is particularly favorable for the heat dissipating body to have a cutout which matches a cutout into the end body and is laterally open.

According to the invention it is particularly favorable for at least two LED chips to emit light having different wavelengths.

According to the invention it is particularly favorable for a cutout of a heat dissipating body of the base body to accommodate a free end of the section of the flexible printed circuit board, at the end of which are formed plug contacts, in particular.

According to the invention it is particularly favorable for each LED chip or all the LED chips to be arranged in a depression of the base body.

According to the invention it is particularly favorable for an end body of the base body and a heat dissipating body of the base body to lie areally one on top of another, in particular in a manner surrounding a common cutout and in particular in U-shaped fashion.

According to the invention it is particularly favorable for all the LED chips to be covered by a converging lens.

According to the invention it is particularly favorable for a plurality of LED chips to be fitted on the inside in a through opening of the flexible printed circuit board that surrounds the LED chips, wherein at least two LED chips can be driven separately and preferably can also emit different wavelengths.

According to the invention it is particularly favorable for each depression in which an LED chip is situated to be covered by an additional lens.

According to the invention it is particularly favorable for a converging lens to cover the LED chips and to surround them in particular in the manner of a hood.

According to the invention it is particularly favorable for the converging lens to have a cutout in which the LED chips are accommodated, and for the converging lens to be sealed with respect to the flexible printed circuit board and for the cutout to be filled with silicone, in particular.

Further advantages, details and features will become apparent from the following description of a plurality of exemplary embodiments with reference to the drawings.

DETAILED DESCRIPTION

Figure 1:
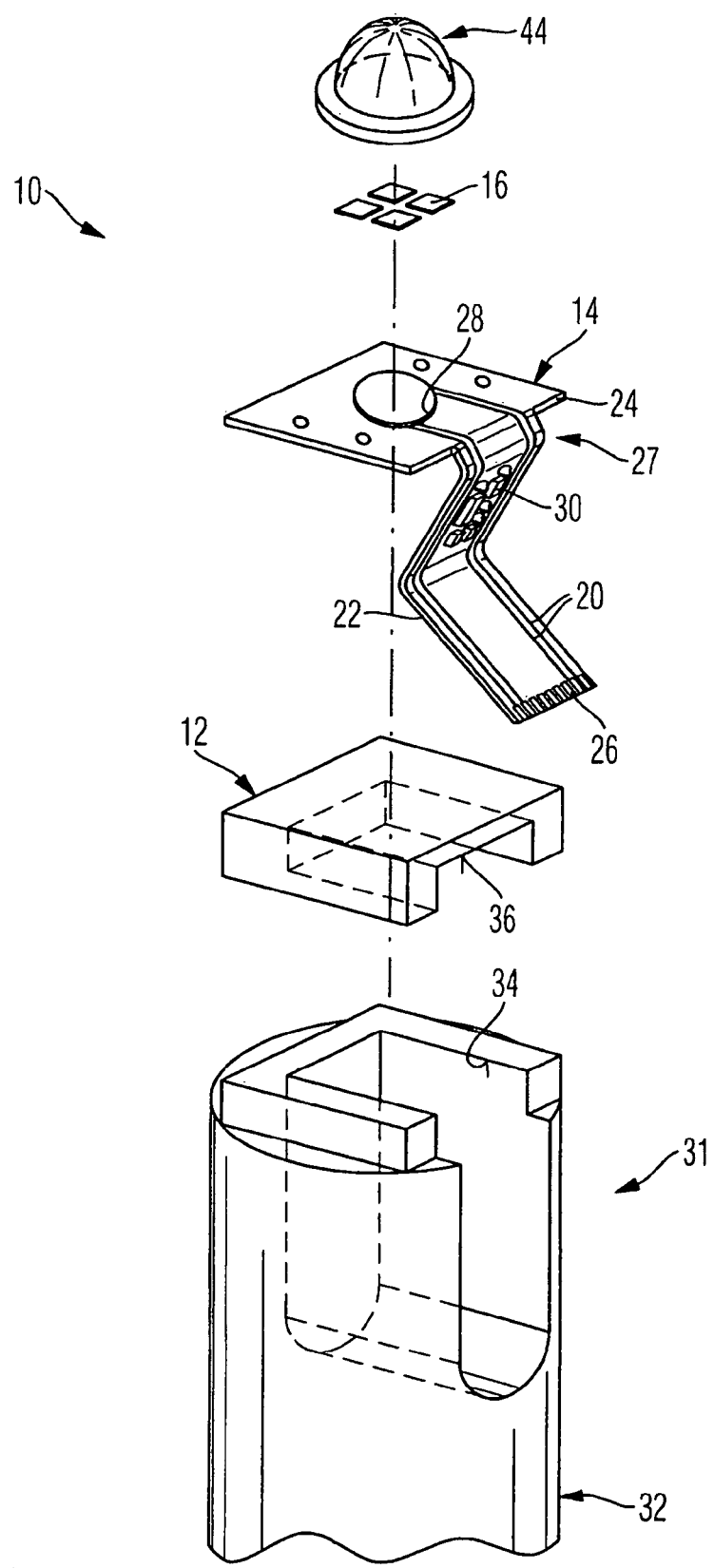
FIG. 1 shows an exploded view of an exemplary embodiment of the semiconductor radiation source of the invention.
Figure 2:
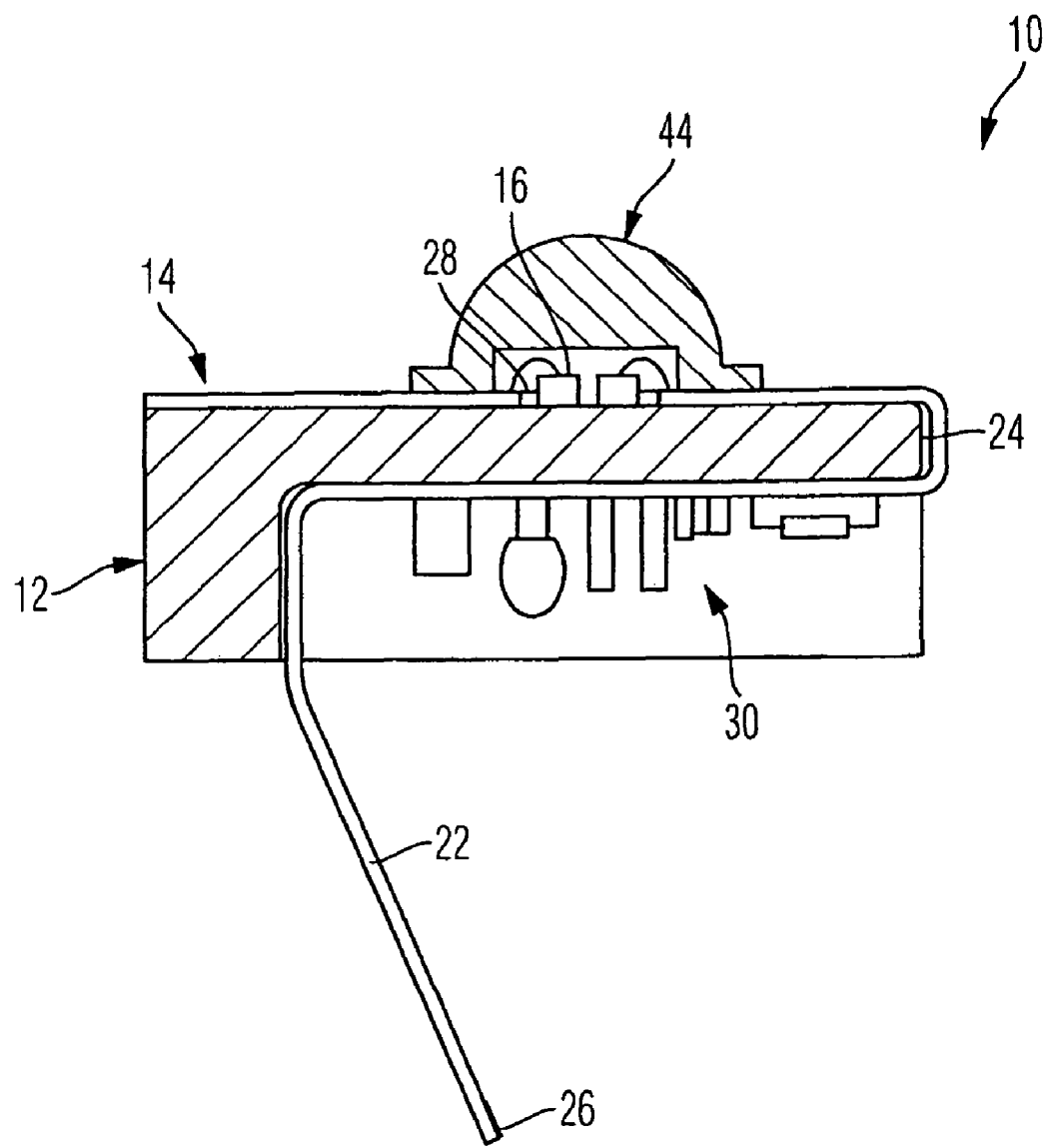
FIG. 2 shows a schematic sectional illustration of the exemplary embodiment of the semiconductor radiation source of the invention.

FIGS. 1 and 2 illustrate an embodiment of a semiconductor radiation source according to the invention. The semiconductor radiation source 10 has an end body 12, which is thermally connected to a heat dissipating body 32. The end body 12 is substantially parallelepipedal and has a cutout 36 at its underside. The cutout 36 is open toward one side. It is surrounded by a central limb and two side limbs of the base body, which lie on limbs of the heat dissipating body 32 that are fit flush with respect to them. A likewise flush cutout 34 facing the cutout 36 is provided into the heat dissipating body 32, wherein the depth of the cutout 34 is significantly deeper than that of the cutout 36.

The base body formed from the end body 12 and the heat dissipating body 32 has a low thermal resistance and accordingly a high thermal conductance, wherein it goes without saying that care is taken to ensure sufficient cooling by means of rear cooling elements (not illustrated here).

The substantially square top side of the end body 12 is covered by a flexible printed circuit board 14 substantially over the whole area. The flexible printed circuit board 14 surrounds a multiple arrangement of LED chips 16 which are fitted on the end body 12 in a thermally conductively connected but electrically insulated manner. This ensures that good cooling of the LED chips is possible. The LED chips are bonded in a manner known per se with connection pads accommodated on the flexible printed circuit board 14. A plurality of conductor tracks 20 extend from there over a connection region 22 of the flexible printed circuit board 14. The flexible printed circuit board 14 is bent over at an edge 24 corresponding to the adjacent edge of the end body 12, to be precise substantially over the entire width of the cutout 36. An angled-away or bent-away section 27 of the flexible printed circuit board 14 is formed as a result of this. Very wide and comparatively short conductor tracks are fitted there, which extend as far as a region 30 at which electrical components are fitted on the flexible printed circuit board.

It is also possible as required to accommodate a voltage transformer there, which ensures that, for the power supplied, comparatively small currents and thus correspondingly reduced line cross sections are necessary in the region of contact areas 26 of the connection region 22 of the flexible printed circuit 14.

In a manner known per se, the region of the LED chips 16 can be covered with a converging lens 44 by way of a spacer ring 28, said lens concentrating the emitted light radiation.

As can be seen from FIG. 1 in comparison with FIG. 2, the connection region 22 of the flexible printed circuit board 14 extends into the cutout 36 of the end body, but also into the cutout 34 of the heat dissipating body, which can be formed for example as an incision 31 into the base body 12. It can be seen from FIG. 2 that the flexible printed circuit board 14 can be bent substantially in U-shaped fashion around the central part of the end body 12, wherein the required electrical components can be accommodated compactly and in protected fashion in the region 30.

The region of the connection zones 26 can also be realized in protected fashion in the region of the cutout 34.

Figure 3:
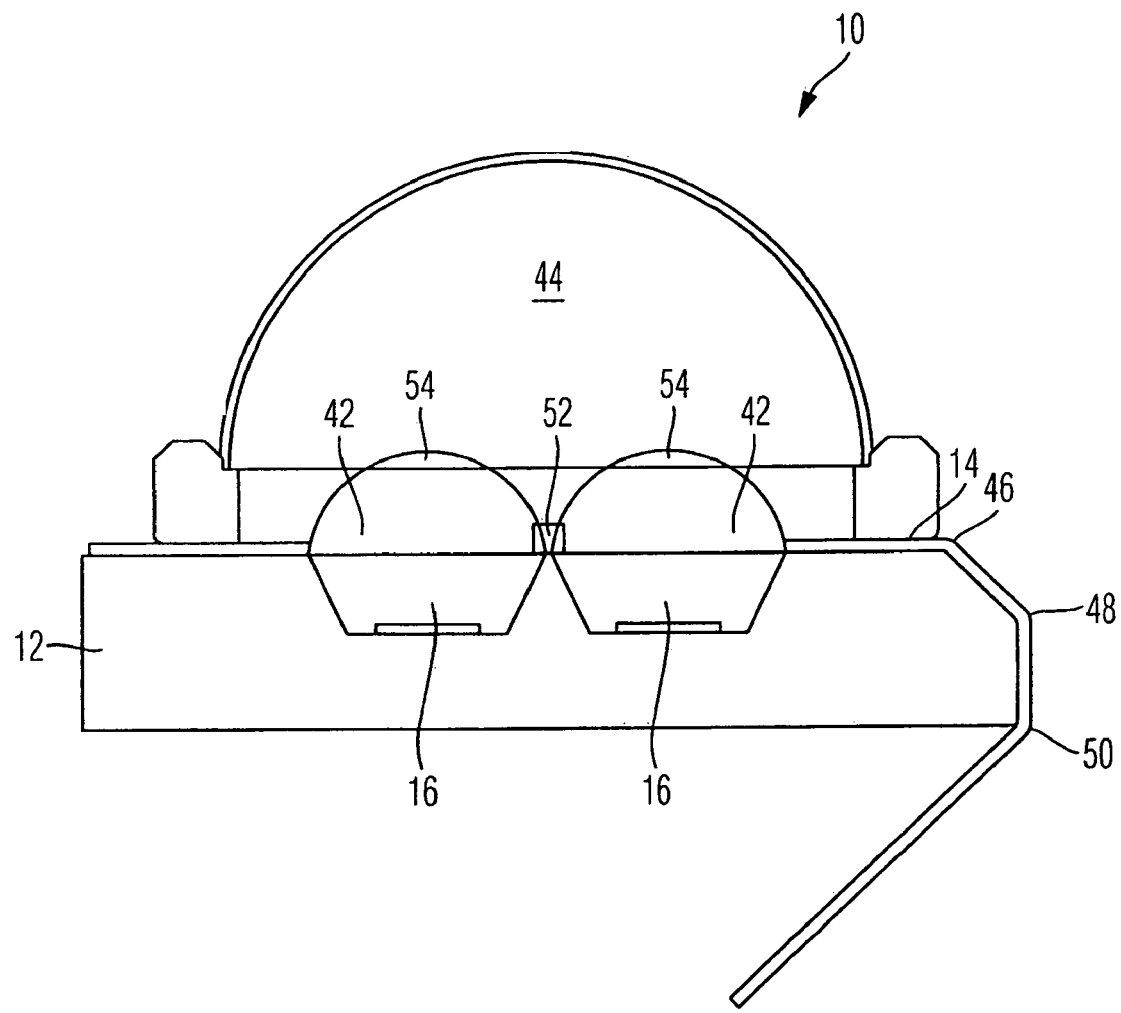
FIG. 3 shows an enlarged illustration of a schematic side view of a further embodiment of a semiconductor radiation source according to the invention.

In FIG. 2 and also in FIG. 3, identical reference symbols indicate parts identical to those in FIG. 1.

FIG. 3 illustrates a further embodiment of the semiconductor radiation source 10 according to the invention. The semiconductor radiation source in accordance with FIG. 3 has a plurality of LED chips 16, of which two LED chips 16 are illustrated in FIG. 3. The LED chips are accommodated in depressions 42 provided in the end body 12 of the base body. In this embodiment, the flexible printed circuit board 14 extends in a manner bent away three times at the locations 46, 48 and 50 along the end body 12 into a cutout 34 formed in the heat dissipating body 32 (not illustrated in FIG. 3).

In the exemplary embodiment illustrated, the LED chips are arranged in a group of four, to be precise centrally below the converging lens 44. In order to improve the light emission, it additionally has individual converging lenses 54, wherein each lens 54 flatly covers the associated depression 42 and extends above the latter substantially in hemispherical fashion.

In the exemplary embodiment illustrated, the individual lenses 54 are optically connected to the common converging lens 44, for which purpose a respective flush depression is formed there, which is intended to serve for improving the light coupling.

It goes without saying that a spaced-apart arrangement can also be chosen instead of this.

A central sensor 52 is furthermore formed in the exemplary embodiment illustrated, which sensor detects the light emission reflected by the irradiated area and regulates the light emission by the LED chips 16.

It goes without saying that the sensor 52 can be surrounded by a black tube in a manner known per se in order to prevent direct exposure to the light emitted by the LED chip 16.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A semiconductor radiation source comprising a base body, at least one LED chip thermally connected to an end side of the base body, and a pliable flexible printed circuit board fitted on the same end side of the base body, wherein the flexible printed circuit board at least partly surrounds the LED chip, has at least one printed-on conductor track (20) electrically connected to the LED chip and, in the peripheral region of the base body, has an angled-away or bent-away section (27) extending at least partly along a side wall of the base body, wherein at least one part of the section (27) of the flexible printed circuit board (14) extends at least partly in lateral cutout (34) into the base body (12), and wherein the bent-away section (27) has a free end which projects freely from the rear side of the base body (12) and is free of electronic components.

2. The semiconductor radiation source as claimed in claim 1, wherein the cutout (34) is formed by a lateral incision (31) or by a through opening (28).

3. The semiconductor radiation source as claimed in claim 1, wherein the section (27) has a width that is smaller than a side length of the base body (12).

4. The semiconductor radiation source as claimed in claim 1, wherein the section (27) extends along at least one part of a rear side—remote from the LED chip (16)—of the base body (12), at the end body thereof.

5. The semiconductor radiation source as claimed in claim 1, wherein the bent-away section (27) in the region of the cutout (34) carries at least one electronic component such as a diode, a resistor or an ASIC, and the at least one electronic components is accommodated in recessed fashion in the cutout (34).

6. The semiconductor radiation source as claimed in claim 1, wherein an end of the base body (12) is thermally connected to a heat dissipating body (32).

7. The semiconductor radiation source as claimed in claim 6, wherein the heat dissipating body (32) has a cutout (34) into which projects the free end of the section.

8. The semiconductor radiation source as claimed in claim 1, wherein a plurality of LED chips (16) are fitted on the base body (12), and wherein at least one LED chip can be driven separately.

9. The semiconductor radiation source as claimed in claim 1, wherein at least two LED chips (16) are provided, which chips emit light having different wavelengths.

10. The semiconductor radiation source as claimed in claim 1, wherein the at least one LED chip (16) is arranged in a depression of the base body.

11. The semiconductor radiation source as claimed in claim 10, wherein the at least one LED chip (16) is covered by a converging lens.

12. The semiconductor radiation source as claimed in claim 11, wherein each depression in which the at least one LED chip is situated is covered by an additional lens.

13. A semiconductor radiation source comprising a base body, at least one LED chip thermally connected to an end side of the base body, and a pliable flexible printed circuit board fitted on the same end side of the base body, wherein the flexible printed circuit board at least partly surrounds the LED chip, has at least one printed-on conductor track (20) electrically connected to the LED chip and, in the peripheral region of the base body, has an angled-away or bent-away section (27) extending at least partly along a side wall of the base body, wherein at least one part of the section (27) of the flexible printed circuit board (14) extends at least partly in a lateral cutout (34) into the base body (12), wherein an end of the base body (12) is thermally connected to a heat dissipating body (32), and wherein the heat dissipating body (32) has a cutout (34) into which projects the free end of the section (27).

14. The semiconductor radiation source as claimed in claim 13, wherein a plurality of LED chips (16) are fitted on the base body (12), and wherein at least one LED chip can be driven separately.

15. The semiconductor radiation source as claimed in claim 13, wherein at least two LED chips (16) are provided, which chips emit light having different wavelengths.

16. The semiconductor radiation source as claimed in claim 13, wherein the at least one LED chip (16) is arranged in a depression of the base body.

17. The semiconductor radiation source as claimed in claim 16, wherein the at least one LED chip (16) is covered by a converging lens.

18. The semiconductor radiation source as claimed in claim 17, wherein each depression in which the at least one LED chip is situated is covered by an additional lens.

19. The semiconductor radiation source as claimed in claim 13, wherein the cutout (34) is formed by a lateral incision (31) or by a through opening (28).

20. The semiconductor radiation source as claimed in claim 13, wherein the section (27) has a width that is smaller than a side length of the base body (12).

21. The semiconductor radiation source as claimed in claim 13, wherein the section (27) extends along at least one part of a rear side—remote from the LED chip (16)—of the base body (12), at the end body thereof.

22. The semiconductor radiation source as claimed in claim 13, wherein the bent-away section (27) in the region of the cutout (34) carries at least one electronic component such as a diode, a resistor or an ASIC, and the at least one electronic component is accommodated in recessed fashion in the cutout (34).

* * * * *